United States Patent [19]

Sabesan

[11] Patent Number: 5,095,123
[45] Date of Patent: Mar. 10, 1992

[54] PROCESS FOR THE PREPARATION OF GLYCOSYL PHOSPHATE TRIESTERS

[75] Inventor: Subramaniam Sabesan, Wilmington, Del.

[73] Assignee: E. I. Du Pont de Nemours and Company, Wilmington, Del.

[21] Appl. No.: 620,252

[22] Filed: Nov. 30, 1990

[51] Int. Cl.$^5$ .................. C07F 9/28; C07H 11/04
[52] U.S. Cl. .................. 549/222; 549/218; 536/117; 536/124
[58] Field of Search ............ 549/218, 222; 536/117, 536/124

[56] References Cited

FOREIGN PATENT DOCUMENTS 61-289086A 12/1986 Japan ..................... 549/222

OTHER PUBLICATIONS

Prihar et al., Carbohyd. Res., 23, 1972, 456–459.
Parihar et al., Biochemistry, vol. 12, 997, 1973.
Inage et al., Chem. Letters 1281 (1982).
Hashimoto et al., J. Chem. Soc. Chem. Commun. 685, 1989.
Aldrich Catalog. p. 506.
H. A. Nunez, et al., Can. J. Chem., vol. 59, 2086(1981).
Yamazaki et al., Can. J. Chem., vol. 59, 2247 (1981).
Y. Watanabe, et al., Tetrahedron Letters, vol. 29, 5763 (1988).
R. R. Schmidt, et al., Tetrahedron Letters, vol. 23, 405 (1982).
A. Granata, et al., Carbohydro. Res., vol. 94, 165 (1981).
M. A. Salam et al., Carbohydrate Res., vol. 90, 83–89 (1981).
C. D. Warren et al., Carbohydrate Res., vol. 64, 43–56 (1978).
L. V. Volkova et al., Carbohydrate Res., vol. 32, 165–166 (1974).
J. Tsai et al., Carbohydrate Res., vol. 64, 297–301 (1978).
H. S. Prihar et al., Carbohydrate Res., vol. 56, 315–324 (1977).

Primary Examiner—Richard L. Raymond
Assistant Examiner—S. Kumar

[57] ABSTRACT

Glycosyl phosphate triesters are prepared by reacting an anomeric mixture of a substituted hexopyranose with 4-N,N-dimethylaminopyridine and diphenyl chlorophosphate wherein using a specific order of addition determines the stereochemistry of the product.

14 Claims, No Drawings

PROCESS FOR THE PREPARATION OF GLYCOSYL PHOSPHATE TRIESTERS

FIELD OF THE INVENTION

This invention relates to a process for the preparation of anomerically enriched glycosyl phosphate triesters which are useful for the preparation of glycosyl dihydrogenphosphate salts.

BACKGROUND OF THE INVENTION

Glycosyl dihydrogenphosphate salts are key intermediates in the biological synthesis of nucleotide sugars that are involved in the assembly of oligosaccharide chains of glycoproteins and glycolipids. Glycosyl dihydrogenphosphate salts in the presence of nucleoside triphosphates are converted to nucleotide sugars by the enzyme nucleotide sugar synthetase. Once formed, these nucleotide sugars function as the donor substrates for glycosyltransferases, which transfer an $\alpha$ or $\beta$ glycosyl residue to growing oligosaccharide acceptor substrates. Enzymatic modification of cell surface oligosaccharide structures using two key tools, the nucleotide sugars and glycosyltransferases, has been shown to be very useful for investigating the role of carbohydrates on these macro molecules. Since several glycosyltransferases have been purified and are commercially available, the preparation of the structurally diverse nucleotide sugar substrates for these enzymes is required for the above mentioned biological investigations.

Many nucleotide sugars have been made enzymatically, and some of these, particularly the natural sugar nucleotides, are also available commercially at a very high cost. Yet, the structural diversity in the glycosyl residues available from these sources is limited, as the enzymatic preparation of nucleotide sugars is dependent on the substrate specificity of the nucleotide-sugar synthetase enzymes.

Chemical methods are an attractive alternative for the preparation of structurally diverse nucleotide sugar derivatives. However, such methods would still require the ready availability of glycosyl dihydrogenphosphate salts that can be coupled to the activated nucleotide mono- or diphosphates. Thus, there is a need for processes for the preparation of glycosyl dihydrogenphosphates and its salts.

Several reports have appeared which disclose the preparation of glycosyl phosphate triesters, or their dihydrogenphosphates and salts of specific sugars using various reagents Prihar, H. S., et al., *Biochemistry*, Vol. 12, 997 (1973) and Nunez, H. A., et al., *Can. J. Chem.*, Vol. 59, 2086 (1981) disclose preparation of glycosyl phosphate esters using O-phenylene phosphorochloridate.

Inage, M., et al., *Chem. Letters*, 1281 (1982) and Yamazaki, T., et al., *Can. J. Chem.* Vol. 59, 2247 (1981) teach preparation of glycosyl phosphate esters using dibenzyl chlorophosphate and butyl lithium.

Dibenzyl phosphorofluoridate synthesis and its use as a phosphorylating agent is disclosed by Watanabe, Y., et al., *Tetrahedron Letters*, Vol. 29, 5763 (1988).

The preparation of D-glucopyranosyl phosphates from D-glucopyranosyl trichloroacetimidates is reported by Schmidt, R. R., et al., *Tetrahedron Letters*, Vol. 23 405 (1982).

Granata, A , et al., *Carbohydr. Res.*, Vol. 94, 165 (1981) disclose the use of diphenyl chlorophosphate and thallium ethoxide or n-butyl lithium in the synthesis of phosphate and related ester derivatives of carbohydrates.

Hashimoto, S., et al., *J. Chem. Soc. Chem. Commun.*, 685 (1989) report a rapid synthesis of 1,2-trans-beta-linked glycosides via benzyl- or benzoyl-protected glycopyranosyl phosphate triesters.

The use of hexopyranosyl acetates and phosphoric acid, as well as the use of glycosyl orthoesters and di-benzyl hydrogenphosphate have also been reported in the preparation of glycosyl phosphate esters.

The object of the present invention is to provide a process for the preparation of glycosyl phosphates in their triester form, preferably anomerically enriched starting with the readily available hexopyranose compounds and the commercially available diphenyl chlorophosphate and 4-N,N-dimethylaminopyridine (DMAP). The glycosyl phosphate triesters prepared via this process can be converted to the natural glycosyl monohydrogenphosphate salts suitable for reaction with activated nucleoside mono- or diphosphates.

SUMMARY OF THE INVENTION

The present invention comprises a process for the preparation of glycosyl phosphate triesters by reacting together a hexopyranose compound, diphenyl chlorophosphate, and 4-N,N-dimethylaminopyridine.

The present invention also provides a process for the preparation of anomerically enriched glycosyl phosphate triesters in which the phosphate group is either cis or trans to the C-2 substituent comprising reacting an anomeric mixture of a hexopyranose compound with diphenyl chlorophosphate and 4-N,N-dimethylaminopyridine in a specific order. The order of addition of the reactants is critical to the determination of the stereochemistry of the product obtained.

In one embodiment of the present invention a process is provided for the preparation of glycosyl phosphate triesters having the phosphate group cis to its neighboring C-2 substituent comprising:

a) reacting 4-N,N-dimethylaminopyridine with an anomeric mixture of a hexapyranose of formula III or IV

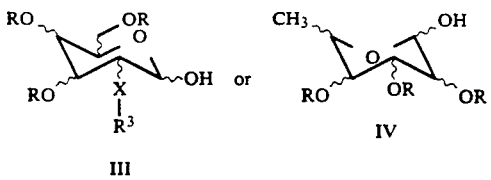

wherein

R is alkyl, aralkyl, aryl, acyl or aroyl; and

X is oxygen and $R^3$ is alkyl, aryl, aralkyl, acyl or aroyl, or X is NH and $R^3$ is acyl, aroyl or alkylcarbamyl;

b) adding diphenyl chlorophosphate to the reaction mixture of a) to yield the desired glycosyl phosphate triester; and c) isolating the desired glycosyl phosphate triester.

In another embodiment of the present invention a process is provided for the preparation of glycosyl phosphate triesters having the phosphate group trans to its neighboring C-2 substituent, comprising:

a) reacting diphenyl chlorophosphate with an anomeric mixture of a hexopyranose of formula IV or V

[Structures V and IV shown]

wherein
R is alkyl, aralkyl, aryl, acyl or aroyl;

b) adding 4-N,N-dimethylaminopyridine to the reaction mixture of a) to yield the desired glycosyl phosphate triester; and c) isolating the desired glycosyl phosphate triester.

DETAILED DESCRIPTION OF THE INVENTION

The present invention provides a process for the preparation of a glycosyl phosphate triester from reaction of an anomeric mixture of a hexopyranose of formula III, IV, or V as defined above, diphenyl chlorophosphate and 4-N,N-dimethylaminopyridine. The glycosyl phospate triesters afforded by the present invention are useful for the synthesis of glycosyl dihydrogenphosphate salts which are commercially valuable and scientifically useful products. The advantage of this process is that the starting material, a hexopyranose compound with a free anomeric hydroxyl group, can be easily obtained, either from the glycosyl halides or by the deprotection of glycosides having a methoxy, allyloxy or benzyloxy group at the anomeric center. In addition, the use of the mild base 4-N,N-dimethylaminopyridine, as compared to strong bases such as n-butyl lithium, allows the utilization of base labile protecting groups, such as acetates, to protect the remaining hexopyranose hydroxyl groups. Furthermore, the phosphorylating conditions are mild, are compatible with a number of functional groups and operate on a wide variety of hexopyranose compounds.

The glycosyl phosphate triesters prepared by the process of the present invention comprise compounds of formula I or II:

[Structures I and II shown]

wherein
R is alkyl, aralkyl, aryl, acyl or aroyl;
X is oxygen and $R^3$ is alkyl, aryl, aralkyl, acyl or aroyl, or X is NH and $R^3$ is acyl, aroyl or alkylcarbamyl;
$R^1$ is H, or $OPO(OR^4)_2$;
$R^2$ is H, or $OPO(OR^4)_2$; and
$R^4$ is aryl;
provided that if one of $R^1$ or $R^2$ is $OPO(OR^4)_2$, then the other is H.

Preferably the alkyl group contains from 1 to 12 carbon atoms for R and $R^3$, and the acyl group of R and $R^3$ contains 1 to 17 carbon atoms. Aralkyl can include for example, but is not limited to, benzyl or diphenylmethyl. The aryl group of the aroyl can include for example, but is not limited to, benzene substituted with at least one alkyl, halogen or methoxy group.

The process of the present invention is preferably used to prepare compounds of formula I or II wherein:
R is benzyl, acetyl or benzoyl;
X is oxygen and $R^3$ is benzyl, acetyl or benzoyl, or X is NH and $R^3$ is acetyl;
$R^1$ is H, or $OP=O$ $(OR^4)_2$;
$R^2$ is H, or $OP=O$ $(OR^4)_2$; and
$R^4$ is phenyl;
provided that if one of $R^1$ or $R^2$ is $OP=O$ $(OR^4)_2$, then the other is H.

The glycosyl phosphate triesters are obtained as the substantially enriched anomer. The term "enriched" is used herein to mean that greater than 50% of the product obtained is of one anomeric form. The term "substantially enriched" is used herein to mean that at least 70% of the product obtained is of one anomeric form. Using the process of the present invention it is possible to obtain the isolated product containing only one of the two possible anomers.

The hexopyranose compounds suitable for use as reactants in the process of the present invention comprise compounds of formula (III), (IV), or (V):

[Structures III, IV, and V shown]

wherein
R is alkyl, aralkyl, aryl, acyl or aroyl;
X is oxygen and $R^3$ is alkyl, aryl, aralkyl, acyl or aroyl; or
X is NH and $R^3$ is acyl, aroyl or alkylcarbamyl.

Preferably the alkyl group of R and $R^3$ contains from 1 to 12 carbon atoms, and the acyl group of R and $R^3$ contains from 1 to 17 carbon atoms. Aralkyl can include for example, but is not limited to, benzyl or diphenylmethyl. The aryl group of the aroyl can include for example, but is not limited to benzene substituted with at least one alkyl, halogen or methoxy group.

Preferred for use herein as reactants are compounds of formula III, IV, or V wherein
R is benzyl, acetyl or benzoyl; and
X is oxygen and $R^1$ is benzyl, acetyl or benzoyl; or X is NH and $R^1$ is acetyl Particularly preferred for use herein are 1) an acetylated pyranose of L-rhamnose, L-fucose, D-glucose, D-galactose, N-acetyl-D-glucosamine or D-mannose; 2) a benzoylated pyranose of glucose or galactose; or 3) a benzylated pyranose of glucose or galactose.

Acetylated and benzoylated hexopyranose compounds for use as reactants are prepared by the silver carbonate catalyzed hydrolysis of the acetylated or benzoylated glycosyl halides in aqueous acetone. The preparation is detailed in (a) McCloskey, C. M.; Coleman, C. H. Org. Synthesis Collective Vol. 1955, 3, 434;

(b) Lemieux, R. U. Methods in Carbohydrate Chemistry , Wolfrom, M. L.; Whistler, R. L. Eds.; Vol. II. Academic Press, New York, 1963, 221; (c) Horton, D. Org. Synthesis 1966, 46, 1; (d) Hewit, G.; Fletcher, Jr., Methods in Carbohydrate Chemistry, Wolfrom, M. L.; Whistler, R. L. Eds.; Vol. II. Academic Press, New York, 1963, 226; each of which is hereby incorporated by reference. The benzyl-hexopyranose of glucose and galactose are prepared by the hydrolysis of the corresponding methyl $\beta$-glycosides as disclosed in (a) Volkova, L. V.; Danilov, L. L.; Evstigneeva, R. P. Carbohydr. Res. 1974, 32, 165; (b) Tsai, J.; Behrman, E. J. Carbohydrate Res. 1978, 64, 297; (c) Salam, M. A.; Behrman, E. J. Carbohydr. Res. 1981, 90, 83; each of which is hereby incorporated by reference. Each of the described procedures yields a product which is an anomeric mixture of the corresponding hexopyranose compound.

The process of the present invention is carried out by combining an anomeric mixture of a hexopyranose with diphenyl chlorophosphate and 4-N,N-dimethylaminopyridine, in a particular order of addition, followed by isolation and purification of the resulting triester product. The order in which the reactants are combined dictates the stereochemistry of the product obtained as shown in the following reaction Scheme I.

reversed: first, the hexopyranose is combined with diphenyl chlorophosphate in a solvent and the 4-N,N-dimethylaminopyridine is then added. Reaction of a D-hexopyranose with stereochemistry as shown for compound 1 in Scheme I, utilizing the reaction conditions of Method A yields, mainly, the $\alpha$-glycosyl phosphate triester in which the phosphate group is cis to its neighboring C-2 substituent. Reaction of compound 2 in Scheme I, utilizing the reaction conditions of Method A yields mainly the $\beta$-glycosyl phosphate triester in which the phosphate group is cis to the C-2 substituent. Thus, reaction of D-hexopyranose compounds under the reaction conditions of Method A yields glycosyl phosphate triesters which have a phosphate group cis to its neighboring C-2 group.

If the order of combination of the reactants is reversed a different product is obtained. Reaction of a D-hexopyranose with stereochemistry as shown for compound 1 in Scheme I, under the reaction conditions of Method B results, mainly, in phosphorylation of the $\beta$-anomeric hydroxyl group yielding a glycosyl phosphate triester with the phosphate group trans to its neighboring C-2 group. Reaction of compound 2 in Scheme I, under the reaction conditions of Method B results mainly in phosphorylation of the $\alpha$-anomeric hydroxyl group yielding a glycosyl phosphate triester with the phosphate group trans to its neighboring C-2

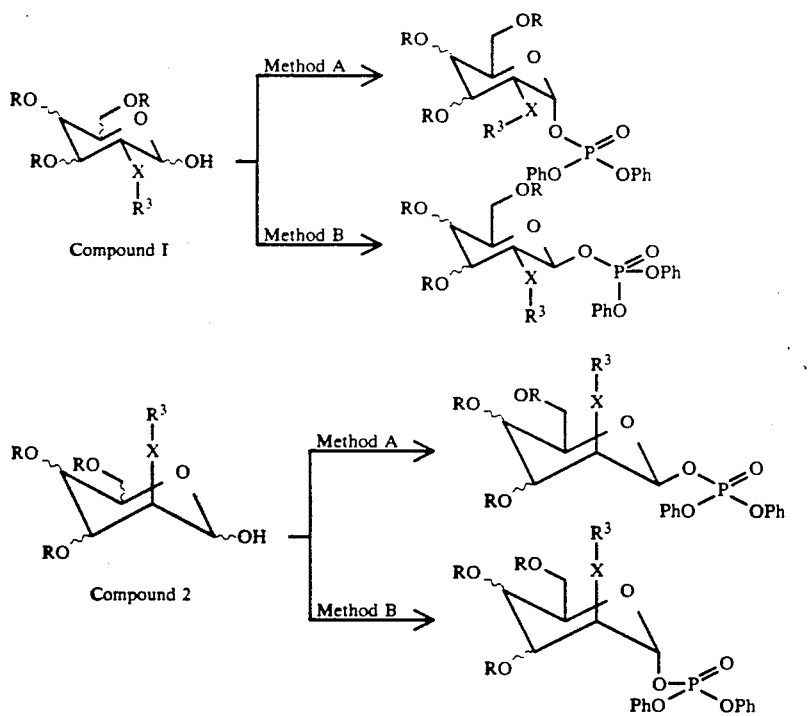

Reaction Scheme I

R is alkyl, aralkyl, aryl, acyl, or aroyl; when X is O, $R^3$ is alkyl, aryl, aralkyl, acyl, or aroyl; or when X is NH, $R^3$ is acyl, aroyl, or alkylcarbamyl.

Scheme I shows the product obtained from the phosphorylation of anomeric mixtures of hexopyranose compounds under two different reaction conditions. In Method A of Scheme I, the hexopyranose is first combined with 4-N,N-dimethylaminopyridine in a solvent and diphenyl chlorophosphate is then added. In Method B of Scheme I, the order of combination of reactants is group. Thus, reaction of D-hexopyranose under the reaction conditions of Method B yields glycosyl phosphate triesters which have a phosphate group trans to its neighboring C-2 group.

In the present invention hexopyranose compounds of formula III, IV or V can be used as reactants to prepare glycosyl phosphate triesters with the phosphate group cis to its neighboring C-2 group. Compounds of formula IV or V can be used as reactants to prepare glycosyl phosphate triesters with the phosphate group trans to its neighboring C-2 group.

The choice of reaction temperature affects the yield of the desired anomer. The optimum reaction temperature varies for each compound and must be determined experimentally, however, utilization of reaction temperatures between about −30° C. and about 25° C. affords product. In general, in the process of the present invention lower temperatures are preferable to higher ones. At higher temperatures unwanted reactions can occur, yields are lower and the product is anomerically less pure. This effect varies with the starting material employed.

More specifically use of temperatures of from about 0° C. to about 25° C. favor formation of the 1,2-cis product. Thus this temperature range is used with Method A wherein the 4-N,N-dimethylaminopyridine is added to the hexopyranose prior to addition of the diphenyl chlorophosphate. Use of temperatures of from about −30° C. to about −1° C. favor formation of the trans anomer, and are best employed with Method B wherein the diphenyl chlorophosphate is added to the hexopyranose prior to the 4-N,N-dimethylaminopyridine. Two exceptions are known to the above general statements as follows: 1) for starting materials of formula III wherein X is NH, use of lower temperatures of from about −30° C. to about −1° C. favors formation of the 1,2-cis product; and 2) for the starting material fucose (formula IV wherein R is acetyl) the α-glycosyl phosphate triester is obtained at any temperature from about −30° C. to about 25° C.

The choice of other reaction parameters is less critical because the process of this invention operates under a variety of conditions. The optimum reaction conditions for each hexopyranose starting material varies and can be determined by experimentation.

Solvents suitable for use in the process of the present invention comprise organic solvents. Halogenated hydrocarbon solvents such as methylene chloride, chloroform, trichloroethylene, tetrachloroethylene, and other similar solvents are suitable. Methylene chloride is preferred for use herein.

The mole ratio of hexopyranose starting material to either 4-N,N-dimethylaminopyridine or diphenyl chlorophosphate suitable for use in the process of the present invention is from about 1:1 to about 1:3 for starting reactant of formula IV or V, or formula III when X is oxygen. Preferred for use herein is a mole ratio of about 1:2. Use of mole ratios in excess of about 1:3 are operable, but constitute a waste of reagent. For starting reactant of formula III, when X is NH, a minimum mole ratio of 1:10 for hexopyranose to diphenyl chlorophosphate and a minimum of 1:20 hexopyranose to 4-N,N-dimethylaminopyridine is required.

The process of the present invention is conducted at ambient pressure. A moisture free inert atmosphere, such as nitrogen or argon is required. Vigorous agitation during the reaction is needed.

Isolation of the desired product is achieved by means common in the art. For example, the desired product can be isolated by high pressure liquid chromatography or column chromatograph. Exemplary specific details are provided in the examples hereinafter.

The glycosyl phospate triesters afforded by the present invention are useful for the synthesis of gycosyl dihydrogenphosphate salts which are commercially valuable and scientifically useful products. The glycosyl phosphate triesters provided by the process of this invention can be converted to glycosyl phosphates by hydrogenation in the presence of platinum(IV)oxide catalyst, followed by treatment with a solution containing methanol-triethylamine-water.

EXAMPLES

In the following examples, all the reagents were purchased from Aldrich Chemical Co. of Milwaukee, Wis. Thin layer chromatography was performed on pre-coated plates of Silica Gel 60 $F_{254}$ (EM Science, Gibbstown, N.J. 08720), and the spots were visualized with a spray containing 5% sulfuric acid in ethanol followed by heating. Column chromatography was done on silica Gel 60 (230–400 mesh, EM Science). $^1$H NMR spectra were recorded at 300 MHz (GE NMR QE-300) and the $^{13}$C- and $^{31}$P NMR spectra were recorded at 75.48 and 121.71 MHz with the same instrument. The spectra of Examples 12a and 12b were obtained in $D_2O$. All others were obtained in $CHCl_3$. The hydrogen and carbon chemical shifts in organic solvents are expressed relative to tetramethylsilane. For solutions of compounds in deuterium oxide, the hydrogen chemical shift values are expressed relative to HOD signal (4.80 ppm at 296 °K), and the carbon chemical shifts are expressed relative to external TMS using the deuterium lock of the spectrometer, which set the chemical shifts of 1,4-dioxane at 66.9 ppm. The $^{31}$P chemical shifts are expressed relative to external $H_3PO_4$.

EXAMPLE 1 a) 2,3,4,6-Tetra-O-acetyl-D-glucopyranose A modified procedure of that reported by McCloskey and Coleman Org. Synthesis Collective Vol. 3, 434 (1955), herein incorporated by reference, was used as follows. A solution of acetobromoglucose (75.0 g) in acetone (150 mL) was added to a vigorously stirred suspension of silver carbonate (35.0 g) in 50% aqueous acetone (340 mL) over a period of 90 min. After 30 min. the solution was filtered over a pad of diatomaceous earth and the filtrate was evaporated to near dryness. The residue was then dissolved in dichloromethane and the organic layer was successively washed with water, ice-cold 0.5M hydrochloric acid and saturated sodium bicarbonate solution. After being dried over anhydrous magnesium sulfate, the solution was evaporated to a dry residue, which was recrystallized (33.1 g) from benzene. The mother liquor upon evaporation afforded an amorphous material (29.7 g). $^1$H NMR in $CDCl_3$ indicated the crystals to be 5:2 mixture of β and α anomers and the foam from the mother liquor to be 1:1 anomeric mixture.

b) Diphenyl (2,3,4,6-tetra-O-acetyl-α-D-glucopyranosyl)phosphate A solution of 2,3,4,6-tetra-O-acetyl-D-gluco-pyranose (2.0 g) in dichloromethane (40 mL) containing 4-N,N-dimethylaminopyridine (1.64 g) was stirred at room temperature for 15 min. and then cooled to −10° C. Diphenylchlorophosphate (2.8 mL) was added in drops and the solution was stirred between −10° C. to 0° C. for 2 hr. and at 4° C. for 1 hr. The reaction mixture was then diluted with dichloromethane and the organic layer was washed with ice cold water, ice cold 0.5M hydrochloric acid and saturated solution of sodium bicarbonate. Chromatographic purification using ethyl acetate-hexane (2:3) afforded the title compound as a syrup, 2.6 g. The structure was confirmed by $^1$H NMR (Table 1).

EXAMPLE 2

Diphenyl (2,3,4,6-tetra-O-benzoyl-α-D-glucopyranosyl)phosphate A solution of 2,3,4,6-tetra-O-benzoyl-D-glucopyranose (prepared by hydrolysis of the corresponding 1-bromide, 3.0 g as described in Hewit, G., Fletcher, Jr., Methods in Carbohydrate Chemistry, Wolfram, M. L.; Whistler, R. L., Eds.; Vol. II, p. 226, Academic Press, New York, NY (1963), herein incorporated by reference), in dichloromethane (40 mL) was cooled to −15° C., and 4-N,N-dimethylaminopyridine (2.4 g) and diphenyl chlorophosphate (4.2 mL) were added. The solution was stirred between −15° C. to −10° C. for 2 hr. The reaction could not be followed by thin layer chromatography as the α-phosphate triester product had nearly the same mobility as the starting material. Work up of the reaction mixture, followed by chromatographic purification (ethyl acetate-hexane=3:8) gave pure α-phosphate triester (2.5 g) along with some impure product (971 mg). The $^1$H NMR was consistent with the structure expected for the title compound (see Table 1).

EXAMPLE 3

Diphenyl (2,3,4,6-tetra-O-benzyl-α-D-glucopyranosyl)phosphate The title compound was prepared from 2,3,4,6-tetra-O-benzyl-α-D-glucopyranose (available from Aldrich Chemical Co.) as described in Example 1b. The $^1$H NMR indicated the crude product to be essentially the desired α phosphate. No attempt was made to further purify this material.

EXAMPLE 4 a) 2,3,4,6-Tetra-O-acetyl-D-galactopyranose Acetobromogalactose (15.0 g) was hydrolyzed according to the procedure described for Example 1a. The product was crystallized (5.4 g) from benzene. The anomeric composition of the crystal was estimated by $^1$H NMR to be 5:2 in favour of β anomer. The weight of the product from the mother liquor was 4.0 g.

b) Diphenyl (2,3,4,6-tetra-O-acetyl-α-D-galactopyranosyl)phosphate 2,3,4,6-Tetra-0-acetyl-D-galactopyranose (3.0 g, recrystallized from benzene) was converted to the title compound as described in Example 1b. The yield of the product was 3.9 g. $^1$H NMR (CDCl$_3$) see Table 1.

EXAMPLE 5

Diphenyl (2,3,4,6-tetra-O-acetyl-β-D-galactopyranosyl)phosphate A solution of 2,3,4,6-tetra-O-acetyl-D-galactopyranose prepared as in Example 4a (2.0 g, recrystallized from benzene) in dichloromethane (40 mL) was cooled to −20° C. Diphenylchlorophosphate (2.8 mL) was added followed by the dropwise addition of a solution of 4-N,N-dimethylaminopyridine (1.64 g) in dichloro-methane (10 mL). The reaction was conducted between −20° C. to −10° C. for 60 min. and the product was isolated as in Example 1b. $^1$H NMR (see Table 1) of the crude product showed it to be predominantly the β phosphate triester. Rapid chromatography afforded the title compound. The yield was 1.65 g. The product underwent anomerization and hydrolysis upon standing at room temperature.

EXAMPLE 6 a) 2-Acetamido-2-deoxy-3,4,6-tri-O-acetyl-D-glucopyranose A solution of 2-acetamido-2-deoxy-3,4,6-tri-O-acetyl-α-D-glucopyranosyl chloride [31.0 g; prepared according to Horton, Org. Synthesis, 46, 1 (1966) herein incorporated by reference]; the crystalized product was contaminated to about 5–10% with 2-acetamido-2-deoxy-1,3,4,6-tetra-O-acetyl-α-D-glucopyranose) in acetonitrile (125 mL) was added to a suspension of silver carbonate (30.0 g) in 50% aqueous acetonitrile (220 mL) over a period of 15 min. and the reaction was continued at room temperature for 16 hr. The reaction mixture was filtered over a pad of Celite and the solution was evaporated to a volume of 150 mL. The solution was filtered again over a pad of Celite and the residue was washed with water (50 mL). The filtrate was extracted with methylene chloride (3×75 mL, most of the desired product remained in the aqueous layer). The organic layer was repeatedly extracted with water (6×100 mL) and all the aqueous solutions were combined. Thin layer chromatography examination of the aqueous layer showed the presence of a homogeneous product, whereas the organic layer contained traces of the title compound and the peracetylated material that was present in the starting material. The aqueous layer was evaporated to dryness, the residue redissolved in dichloromethane, then dried over anhydrous magnesium sulfate and evaporated to obtain an amorphous product (24.0 g). Examination by $^1$H NMR confirmed the structure of the product to be the titled compound containing greater than 90% of the α-anomer.

b) Diphenyl (2-acetamido-2-deoxy-3,4,6-tri-O-acetyl-α-Dglucopyranosyl)-phosphate To a solution of 2-acetamido-2-deoxy-3,4,6-tri-O-acetyl-D-glucopyranose (Example 6a, 5.0 g) in dichloromethane (400 mL) at −30° C. containing 4-N,N-dimethylaminopyridine (15.0 g), diphenyl chloro-phosphate (20.0 mL) was added and the reaction mixture was stirred between −30 to −25° C. for 2 hr. Examination of the reaction mixture showed a single major product (the title compound) along with traces of a minor product. The reaction mixture was worked up as described above in Example 1b and purified by chromatography using ethyl acetate-hexane (3:2) as eluant. The yield of the amorphous material was 5.2 g. ($^1$H NMR, see Table 1).

EXAMPLE 7 a) 2,3,4,6-Tetra-O-acetyl-D-mannopyranose Acetobromomannose (115.0 g) upon hydrolysis according to the procedure described in Example 1a afforded crude syrup (87.0 g). Crystallization of 59.0 g of this syrup from benzene afforded 29.0 g of crystals. About 25.0 g of foam was obtained from the mother liquor. $^1$H NMR spectrum of the crystal and the foam indicated more than 80% of the anomer was in the α pyranose form, which increased further upon the addition of 4-N,N-dimethylaminopyridine.

b) Diohenyl (2,3,4.6-tetra-O-acetyl-α-D-mannopyranosyl)phosphate To a solution of 2,3,4,6-tetra-O-acetyl-D-mannopyranose (3.0 g) in dichloromethane (50 mL) at −30° C., a solution of 4-N,N-dimethylaminopyridine (2.4 g) and diphenyl chlorophosphate (4.2 mL) in dichloromethane (20 mL) was added over a period of 30 min. After 1 hr., the reaction mixture was warmed to −20° C. and then maintained between 0 and −10° C. for 2 hr. The reaction mixture was worked up and purified by chromatography using ethyl acetate/hexane (3:8) as eluant. The yield of the α-phosphate triester was 4.7 g. $^1$H NMR (see Table 1).

EXAMPLE 8

To a solution of 2,3,4,6-tetra-O-acetyl-β-D-mannopyranosyl)phosphate To a solution of 2,3,4,6-tetra-O-acetyl-D-mannopyranose prepared as in Example 7a (3.0 g) in dichloromethane (50 mL) at room temperature containing 4-N,N-dimethylamino-pyridine; (2.4 g), a solution of diphenyl chlorophosphate (4.2 mL) in dichloromethane (20 mL) was added over a period of 60 min. After 2 hr., the reaction was worked up and the products were isolated by chromatography using ethyl acetate/hexane (3:8) as eluant. After elution of the less polar α-phosphate triester (937 mg), the eluant was changed to ethyl acetate/hexane (2:3) to get the major β-phosphate (3.85 g). The structure of the title compound was confirmed by NMR (see Table 1). The NMR data obtained for the α-phosphate triester was identical to that obtained for the product of Example 7b.

EXAMPLE 9 a) 2,3,4-Tri-O-acetyl-L-rhamnopyranose L-Rhamnose (46.0 g) was acetylated with acetic anhydride in pyridine and the crude acetate obtained was treated with 30% hydrogen bromide in acetic acid. The crude bromide was hydrolyzed as described in the procedure of Example 1a. Following hydrolysis and filtration over diatomaceous earth, the filtrate was concentrated during which crystals started to appear. These were filtered and washed with ice cold water (the title compound was found to be appreciably soluble in water) to obtain 17.0 g of solid (residue 1). The filtrate was extracted with dichloromethane and the dichloromethane layer was washed with ice-cold hydrochloric acid and saturated sodium bicarbonate solution. Evaporation of the solvent afforded 32.0 g of solid (residue 2). $^1$H NMR of residues 1 and 2 indicated to be an anomeric mixture with greater than 75% α anomer.

b) Diohenyl (2,3,4-tri-O-acetyl-α-D-rhamnopyranosyl)phosphate 2,3,4-Tri-O-acetyl-L-rhamnopyranose (3.0 g) was converted to the phosphate triester according to the procedure described in Example 7b. The yield of the purified product was 3.5 g. The structure was confirmed by NMR (Table 1).

EXAMPLE 10

Diphenyl (2,3,4-tri-O-acetyl-β-L-rhamnopyranosyl)phosphate 2,3,4-Tri-O-acetyl-L-rhamnopyranose prepared as in Example 9a (1.0 g) was converted to the phosphate according to the procedure described in Example 8. The yield of the β-phosphate triester (the title compound) was 1.1 g and that of the α-phosphate triester was 380 mg. The structures were confirmed by NMR (Table 1, shows data only for the title compound; the data obtained for the α-phosphate triester was identical to that obtained for the product of Example 9b).

EXAMPLE 11 a) 2,3,4-Tri-O-acetyl-L-fucopyranose L-Fucose (46.0 g) was converted to 2,3,4-tri-O-acetyl-L-fucopyranose according to the procedure described in Example 9a for 2,3,4-tri-O-acetyl-L-rhamnopyranose. The crude syrupy product contained about 10% of the furanose derivative in addition to the pyranose (α anomer about 48%, β anomer about 41%). Upon standing in the refrigerator, pure pyranose crystallized out, which was washed with ice-cold ethanol-hexane to give colorless crystals (20.5 g). $^1$H NMR showed the crystals to be greater than 90% of the α anomer.

b) Diphenyl(2,3,4-tri-O-acetyl-α-D-fucopyranosyl)-phosphate: 2,3,4-Tri-O-acetyl-L-fucopyranose (2.0 g) was converted to the phosphate triester according to the procedure described in Example 4b. The yield of product was 2.0 g and the structure was confirmed by NMR (Table 1).

UTILITY EXAMPLE

Procedure for the deprotection of glycosyl phosphate triesters The phenyl protecting group at the phosphate and the acetate groups on the pyranosyl residue for the relevant compounds were removed by the following procedure illustrated for the preparation of triethylammonium α-D-glucopyranosyl monohydrogenphosphate.

Triethylammonium α-D-glucopyranosyl monohydrogenphosphate A solution of the compound of Example 1b (500 mg) in ethyl acetate-ethanol (1:1, 10 mL) was hydrogenated (55 psi pressure) in the presence of platinum(IV) oxide catalyst (10 mg) for 16 hr. The completion of the reaction was evidenced by the disappearance of the UV active starting and intermediate phosphate diesters. The catalyst was filtered and the solution was neutralized with triethyl amine. Evaporation of the solvent afforded a syrup. The structure of this product as mono-triethylammonium (2,3,4,6-tetra-O-acetyl-α-D-glucopyranosyl)-monohydrogenphosphate was confirmed by $^1$H NMR (see Example 12a in Table 1).

The above product was dissolved in a mixture of methanol-triethylamine-water (2:1:1, 20 mL) and then left at 0° C. for 5 days. The solution was then evaporated to dryness and the residue was redissolved in water. This was then lyophilized and the procedure was repeated once. The structure of the title compound was evident from its $^1$H NMR (see Example 12b in Table 1).

TABLE 1

| | NMR paramaters of hexopyranosyl phosphates | | | | | | | |
|---|---|---|---|---|---|---|---|---|
| Example | Atoms | 1 | 2 | 3 | 4 | 5 | 6 | 6B | 31p |
| 1 | 1$_H$a | 6.06 | 5.02 | 5.52 | 5.13 | 4.07 | 4.18 | 3.88 | |
|   | 13$_C$a | 95.0 | 69.35 | 69.81 | 67.6 | 76.6 | 61.1 | | −13.48 |
| 2 | 1$_H$a | 6.42 | 5.58 | 6.28 | 5.83 | 4.59 | 4.51 | 4.39 | |
|   | 13$_C$a | 95.4 | 71.0 | 69.8 | 68.7 | 70.4 | 62.3 | | −13.44 |
| 3 | 1$_H$a | 6.06 | 3.63 | 3.88 | 3.75 | 3.75 | 3.63 | 3.35 | |
|   | 13$_C$a | 96.9 | 78.9 | 80.9 | 76.4 | 75.1 | 67.4 | | −14.63 |
| 4 | 1$_H$a | 6.12 | 5.26 | 5.38 | 5.48 | 4.35 | 4.08 | 3.92 | |
|   | 13$_C$a | 95.7 | 66.9 | 68.8 | 67.4 | 77.2 | 61.0 | | 13.3 |
| 5 | 1$_H$a | 5.45 | 5.35 | 5.04 | 5.43 | 4.13 | 4.13 | 4.06 | |
| 6 | 1$_H$a | 5.95 | 4.41 | 5.25 | 5.18 | 4.05 | 4.16 | 3.89 | |
|   | 13$_C$a | 97.4 | 52.3 | 70.1 | 67.5 | 70.3 | 61.3 | | −13.85 |
| 7 | 1$_H$a | 5.87 | 5.3 to 5.4 | | | 4.08 | 4.20 | 3.93 | |
|   | 13$_C$a | 96.1 | 68.7 | 68.2 | 65.4 | 70.8 | 61.8 | | −13.96 |
| 8 | 1$_H$a | 5.59 | 5.49 | 5.07 | 5.25 | 3.78 | 4.27 | 4.12 | |
|   | 13$_C$a | 94.8 | 68.1 | 70.1 | 65.7 | 73.2 | 62.1 | | −13.64 |

TABLE 1-continued

| Example | Atoms | NMR paramaters of hexopyranosyl phosphates | | | | | | | 31p |
|---|---|---|---|---|---|---|---|---|---|
| | | 1 | 2 | 3 | 4 | 5 | 6 | 6B | |
| 9 | 1Ha | 5.80 | 5.31 | 5.31 | 5.09 | 3.95 | 1.11 | | |
| | 13Ca | 96.4 | 69.2 | 68.9 | 68.3 | 70.4 | 17.2 | | −13.83 |
| 10 | 1Ha | 5.55 | 5.48 | 5.00 | 5.07 | 3.62 | 1.24 | | |
| | 13Ca | 94.8 | 68.6 | 70.4 | 70.1 | 71.5 | 20.5 | | −13.55 |
| 11 | 1Ha | 6.07 | 5.21 | 5.35 | 5.27 | 4.17 | 1.0 | | |
| | 13Ca | 96.3 | 67.1 | 67.4 | 67.3 | 70.6 | 20.4 | | −13.2 |
| 12a | 1H | 5.71 | 5.07 | 5.51 | 5.17 | 4.42 | 4.42 | 4.20 | |
| 12b | 1Hc | 5.45 | 3.51 | 3.8 | 3.42 | 3.8 | 3.7 | 3.7 | |
| | 13Cc | 94.8 | 71.7 | 72.6 | 69.6 | 72.9 | 60.7 | | 0.939 |

What is claimed is:

1. A process for the selective preparation of a substantially enriched α or β anomer of a glycosyl phosphate triester comprising reacting a hexopyranose of formula III, IV, or V

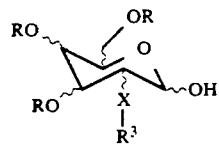

III

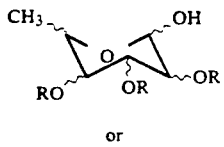

IV or

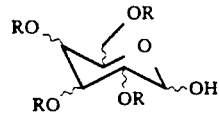

V wherein
R is $C_1-C_{12}$ is alkyl, aralkyl, hydrocarbyl aryl, hydrocarbyl acyl, or $C_1-C_{17}$ hydrocarbyl aroyl; and
X is oxygen and $R^3$ is $C_1-C_{12}$ is alkyl, hydrocarbyl aryl, hydrocarbyl aralkyl, $C_1-C_{17}$ acyl or hydrocarbyl aroyl, or X is NH and $R^3$ is $C_1-C_{17}$ acyl or hydrocarbyl aroyl or
with 4-N,N-dimethylaminopyridine and diphenyl chlorophosphate.

2. A process for the preparation of a substantially enriched anomer of a glycosyl phosphate triester in which the phosphate group is cis to the C-2 substituent comprising:
a) reacting 4-N,N-dimethylaminopyridine with an anomeric mixture of a hexopyranose of formula III or IV;

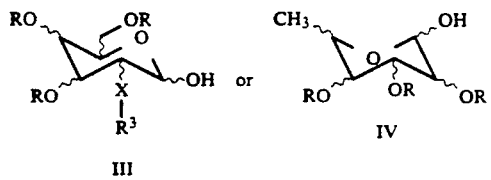

wherein
R is $C_1-C_{12}$ alkyl hydrocarbyl aralkyl, hydrocarbyl aryl, $C_1-C_{17}$ acyl or hydrocarbyl aroyl; and
X is oxygen and $R^3$ is $C_1-C_{12}$ alkyl, hydrocarbyl aryl, hydrocarbyl aralkyl, $C_1-C_{17}$ acyl or hydrocarbyl aroyl, or X is NH and $R^3$ is $C_1-C_{17}$ acyl or hydrocarbyl aroyl b) adding diphenyl chlorophosphate to the reaction mixture of a) to yield the desired glycosyl phosphate triester; and
c) isolating the desired glycosyl phosphate triester.

3. A process for the preparation of a substantially enriched anomer of a glycosyl phosphate triester in which the phosphate group is trans to the C-2 substituent comprising:
a) reacting diphenyl chlorophosphate with an anomeric mixture of a hexopyranose of formula IV or V;

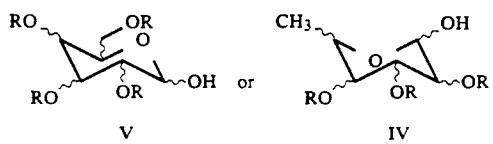

wherein R is $C_1-C_{12}$ alkyl, hydrocarbyl aralkyl, hydrocarbyl acyl or $C_1-C_{17}$ hydrocarbyl aroyl;
b) adding 4N,N-dimethylaminopyridine to the reaction mixture of a) to yield the desired glycosyl phosphate triester; and
c) isolating the desired glycosyl phosphate triester.

4. The process of claim 1, 2 or 3 wherein the glycosyl phosphate triester comprises a compound of formula I or II:

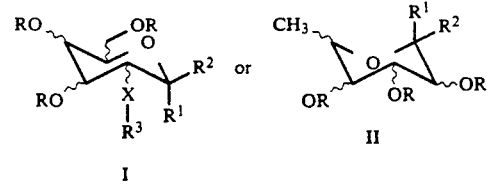

wherein
R is alkyl, aralkyl, aryl, acyl or aroyl;
X is oxygen and $R^3$ is alkyl, aryl, aralkyl, acyl, or aroyl; or X is NH and $R^3$ is acyl, aroyl, or alkylcarbamyl;
$R^1$ is H, or $OPO(OR^4)_2$;
$R^2$ is H, or $OPO(OR^4)_2$; and
$R^4$ is hydrocarbyl aryl;
provided that if one of $R^1$ or $R^2$ is $OPO(OR^4)_2$, then the other is H.

5. The process of claim 4 wherein the triester comprises a compound of formula I or II wherein
R is benzyl, acetyl or benzoyl;
X is oxygen and $R^3$ is acetyl or benzoyl, or X is NH or $R^3$ is acetyl;
$R^1$ is H, or $OP=O(OR^4)_2$;

$R^2$ is H, or $OP=O(OR^4)_2$; and
$R^4$ is phenyl;
provided that if one of $R^1$ or $R^2$ is $OP=O(OR^4)_2$, then the other is H.

6. The process of claim 1, 2 or 3 wherein the hexopyranose comprises 1) an acetylated pyranose of L-rhamnose, L-fucose, D-glucose, D-galactose, N-acetyl-D-glucosamine or D-mannose; 2) a benzoylated pyranose of glucose or galactose; or 3) a benzylated pyranose of glucose or galactose.

7. The process of claim 1, 2 or 3 conducted at a temperature of from about $-30°$ C. to about 25° C.

8. The process of claim 3 wherein the steps a) and b) are conducted at a temperature of from about $-30°$ C. to about $-1°$ C.

9. The process of claim 2 wherein steps a) and b) are conducted at a temperature of from about 0° C. to about 25° C. when X is oxygen and at a temperature of from about $-30°$ C. to about $-1°$ C. when X is NH.

10. The process of claim 1, 2 or 3 conducted in a halogenated hydrocarbon solvent.

11. The process of claim 1, 2 or 3 conducted in methylene chloride.

12. The process of claim 1, 2, or 3 wherein for formula IV or V, or for formula III when X is oxygen, the mole ratio of hexopyranose to either 4-N,N-dimethylamino-pyridine or diphenyl chlorophosphate is from about 1:1 to about 1:3.

13. The process of claim 12 wherein said mole ratio is about 1:2.

14. The process of claim 1 or 2 wherein for formula III when X is NH the mole ratio of hexopyranose to 4-N,N-dimethylaminopyridine is about 1:20 and to diphenyl chlorophosphate is about 1:10.

* * * * *